(12) United States Patent
Van Helvoort

(10) Patent No.: US 10,702,212 B2
(45) Date of Patent: Jul. 7, 2020

(54) MAGNETIC RESONANCE EXAMINATION SYSTEM WITH MOTION DETECTION

(71) Applicant: KONINKLIJKE PHILIPS N.V., Eindhoven (NL)

(72) Inventor: Marinus Johannes Adrianus Maria Van Helvoort, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 11 days.

(21) Appl. No.: 14/408,312

(22) PCT Filed: Jun. 17, 2013

(86) PCT No.: PCT/IB2013/054960
§ 371 (c)(1),
(2) Date: Dec. 16, 2014

(87) PCT Pub. No.: WO2013/190451
PCT Pub. Date: Dec. 27, 2013

(65) Prior Publication Data
US 2015/0150511 A1    Jun. 4, 2015

Related U.S. Application Data

(60) Provisional application No. 61/662,503, filed on Jun. 21, 2012.

(51) Int. Cl.
*A61B 5/00* (2006.01)
*G01R 33/565* (2006.01)
(Continued)

(52) U.S. Cl.
CPC .............. *A61B 5/721* (2013.01); *A61B 5/055* (2013.01); *G01R 33/30* (2013.01);
(Continued)

(58) Field of Classification Search
None
See application file for complete search history.

(56) References Cited

U.S. PATENT DOCUMENTS 6,612,992 B1 * 9/2003 Hossack ................. A61B 8/12
600/467
7,657,299 B2    2/2010 Huizenga et al.
(Continued)

FOREIGN PATENT DOCUMENTS

WO    2011033422 A1    3/2011

OTHER PUBLICATIONS

Buikman, D. et al "The RF Coil as a Sensitive Motion Detector for Magnetic Resonance Imaging" Magnetic Resonance Imaging, vol. 6, No. 3, May 1988, pp. 281-289.

*Primary Examiner* — Joseph M Santos Rodriguez

(57) ABSTRACT

A magnetic resonance examination system includes an RF arrangement with an RF antenna to acquire magnetic resonance signals from an object to be examined. A motion sensing arrangement detects motion information of the object. The motion sensing arrangement is provided with one or more RF antenna motion sensors mounted on the RF antenna and one or more object motion sensors to be attached to the object. In an example the motion sensors are integrated devices having motion sensitivity along three independent axes.

16 Claims, 1 Drawing Sheet

(51) Int. Cl.
*A61B 5/055* (2006.01)
*G01R 33/30* (2006.01)
*G01R 33/34* (2006.01)
*G01R 33/385* (2006.01)
*G01R 33/54* (2006.01)
*G01R 33/563* (2006.01)

(52) U.S. Cl.
CPC ... *G01R 33/34046* (2013.01); *G01R 33/3852* (2013.01); *G01R 33/543* (2013.01); *G01R 33/563* (2013.01); *G01R 33/56509* (2013.01); *A61B 5/004* (2013.01); *A61B 5/0555* (2013.01)

(56) References Cited

U.S. PATENT DOCUMENTS

| | | | |
|---|---|---|---|
| 2003/0016015 A1* | 1/2003 | Eggers | G01R 33/28 324/307 |
| 2005/0107685 A1 | 5/2005 | Seeber | |
| 2008/0081980 A1 | 4/2008 | Maschke | |
| 2009/0289747 A1* | 11/2009 | Duraffourg | H03H 3/0073 333/219.2 |
| 2010/0156421 A1* | 6/2010 | Sukkau | G01R 33/3415 324/318 |
| 2011/0204891 A1* | 8/2011 | Drake | G01N 24/084 324/309 |
| 2014/0073904 A1 | 3/2014 | Biber | |

* cited by examiner

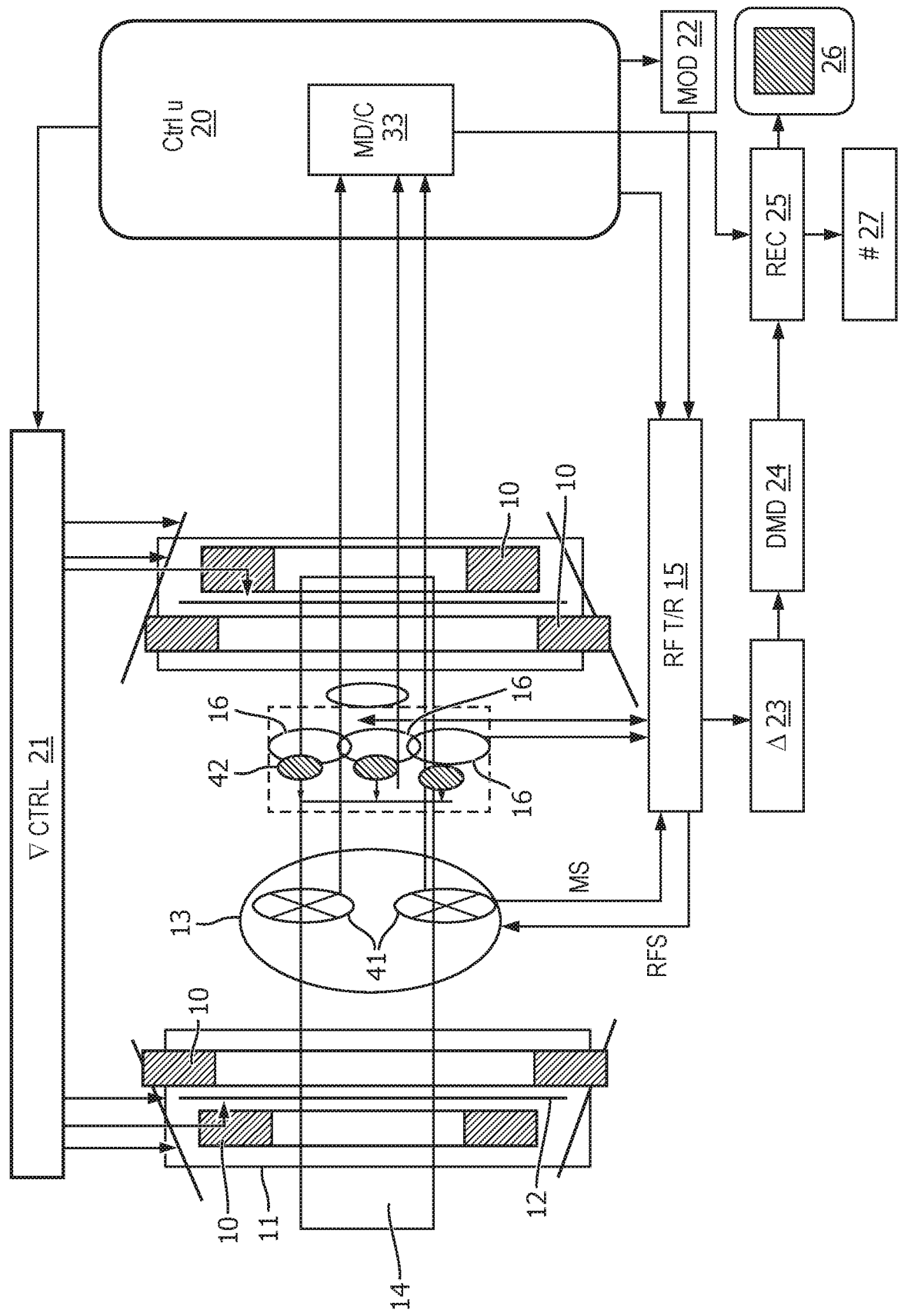

MAGNETIC RESONANCE EXAMINATION SYSTEM WITH MOTION DETECTION

FIELD OF THE INVENTION

The invention pertains to a magnetic resonance examination system with a motion sensing arrangement to detect motion information of the object to be examined.

BACKGROUND OF THE INVENTION

Such a magnetic resonance examination system is known from the international application WO2011/033422.

The known magnetic resonance examination system includes a motion sensor, e.g. a compression sensor, an acceleration sensor or a position sensor. The motion sensor generates motion signals that can be used for motion correction in an MR imaging procedure. Optionally, several motion sensors may be integrated into an RF coil unit of the magnetic resonance examination system. Motion information collected by different sensors may be combined in a motion model that is used for motion compensation. In one embodiment the RF coil unit with the integrated motion sensor is positioned directly on the body of a patient to be examined in order to detect motion of the body in the region from which the magnetic resonance signals are acquired.

SUMMARY OF THE INVENTION

An object of the invention is to provide a magnetic resonance examination system with a motion detection arrangement that provides motion information at a higher accuracy.

This object is achieved by a magnetic resonance examination system according to the invention comprising an RF arrangement with an RF antenna to acquire magnetic resonance signals from an object to be examined, a motion sensing arrangement to detect motion information of the object, a data processor to reconstruct an magnetic resonance image from the magnetic resonance signals, the RF arrangement being coupled to the data processor to apply the magnetic resonance signals to the data processor, the motion sensing arrangement being coupled to the data processor to apply the detected motion information to the data processing unit, wherein the motion sensing arrangement is provided with one or more RF antenna motion sensors mounted on the RF antenna and one or more object motion sensors to be attached to the object.

The motion sensing arrangement comprises both RF antenna motion sensors mounted on the RF antenna as well as object motion sensors to be attached to the object. Notably, the object motion sensors are to be placed on or to be attached to the body of the patient to be examined. The RF antenna motion sensors provide information on the motion of the RF antenna. The object motion sensors provide information on the motion of the object. Thus, the RF antenna motion sensors and the object motion sensors together provide information on the relative position of the RF antenna and the object. This allows accurate determination of the motion of both the object and the RF antenna even when the RF antenna and the object each move in different manners. Thus, motion is accurately determined also when the RF antenna does not rigidly move with the motion of the object. This occurs when the RF antenna is for example an RF receiver coil which is deformable or semi-rigid which does not precisely conform to the motion of the patient to be examined, but also does not remain fixedly mounted to the structure of the magnetic resonance examination system.

The motion sensing arrangement further includes an arithmetic unit to compute the motion of both the RF antenna and the object on the basis of the detected motion by the RF antenna motion sensors and the object motion detection sensors, respectively. Thus, the motion information is computed by the arithmetic unit.

The RF arrangement has an output coupled to the data processor to apply the received magnetic resonance signals to the data processor. The data processor is provided with a motion correction module. The motion correction module corrects the magnetic resonance signals for the detected motion. The data processor further includes a reconstruction module to reconstruct an magnetic resonance image on the basis of the magnetic resonance signals, e.g. by way of a fast-Fourier transform (FFT). These motion-corrected magnetic resonance signals are then fed into a reconstructor which reconstructs the magnetic resonance image from the motion-corrected magnetic resonance signals. This reconstructed magnetic resonance image has no or only few residual motion artefacts. Alternatively, the magnetic resonance signals can be fed into the reconstructor which reconstructs the magnetic resonance image from the magnetic resonance signals. The motion correction module is arranged to receive the magnetic resonance image in which motion artefacts occur and on the basis of the motion information corrects the received magnetic resonance image to the reconstructed magnetic resonance image in which no or only few residual motion artefacts occur.

In a preferred embodiment of the invention, the motion sensors are provided with integrated circuit devices having motion sensitivity in one or more, notably two or three, independent, axes. The integrated circuit is based on microelectronics with smallest details of less than 100 nm, or even in nano-electonics. Motion detection can be realized e.g. with MEMS (micro-electro-mechanical switches) as well. For example the independent axes are mutually transverse or orthogonal. Notably micro/nano-electronic devices that are sensitive to roll and pitch rotations can be employed in combination with micro/nano-electronic devices that are sensitive to yaw rotations. Thus, on the basis of miniature electronic devices sensing of motion along three or even nine axes, i.e. in a volume, is achieved.

In another embodiment of the invention, the RF antenna is formed by an RF receiving coil that has an structure of electrically conductive coil elements, e.g. forming one or more coil loops, which can pick up magnetic flux of magnetic resonance signals. The RF antenna motion sensors, e.g. comprising micro/nano-electronic devices are mounted rigidly to or even integrated in the structure of the RF receiving coil. It does not really matter exactly where the RF antenna motion sensors are located in or on the structure of the RF receiving coil, as long as the connection is rigid, i.e. loop and sensor follow the same trajectory during motion. In this way the RF antenna motion sensors accurately sense the movement, position and shape of the coil.

In a further embodiment the RF receiving coil is provided with flexible receiver elements to pick-up magnetic resonance signals. The RF antenna motion sensors are integrated in the flexible receiver elements. This enables to track the deformation of the flexible receiver elements in a direct manner. For example, the RF receiving coil has a semi-rigid part with coil elements and RF antenna motion sensors tracking the coil motion and a flexible part with coil elements and object motion sensors on top of the patient following patient motion. Notably, the motion signals output by the motion sensors which are mounted in or on an individual flexible receiver element represent directly the shape of the flexible receiver element. Successive sensing by the motion sensors of the flexible receiver element enables to track changes of the shape of that receiver element, i.e. to track the deformation of the flexible receiver element. In a semi rigid coil one RF antenna sensor at one of the sides of the RF receiving coils would already bring improvement. Typically during breathing in the centre of the patient's chest is lifted, lifting the centre of the coil (but remain at the same relative distance). The edges of the coil however move away from the patient body, i.e. distance and element orientation changes. Typically motion detection is required with respect to three axis: movement in x-direction, movement in y-direction and roll over the z-axis. (z-axis is in the longitudinal direction of the magnet of the magnetic resonance examination system). If coil elements become very flexible, like 'non-elastic wearable' sensors at various positions are required, in practice four RF antenna motion sensors on the RF receiving coil achieves good results.

These and other aspects of the invention will be elucidated with reference to the embodiments described hereinafter and with reference to the accompanying drawing wherein

BRIEF DESCRIPTION OF THE DRAWINGS

The FIGURE shows diagrammatically a magnetic resonance imaging system in which the invention is used.

DETAILED DESCRIPTION OF THE EMBODIMENTS

The FIGURE shows diagrammatically a magnetic resonance imaging system in which the invention is used. The magnetic resonance imaging system includes a set of main coils 10 whereby the steady, uniform magnetic field is generated. The main coils are constructed, for example in such a manner that they enclose a tunnel-shaped examination space. The patient to be examined is placed on a patient carrier 14 which is slid into this tunnel-shaped examination space. The magnetic resonance imaging system also includes a number of gradient coils 11, 12 whereby magnetic fields exhibiting spatial variations, notably in the form of temporary gradients in individual directions, are generated so as to be superposed on the uniform magnetic field. The gradient coils 11, 12 are connected to a gradient control 21 which includes one or more gradient amplifier and a controllable power supply unit. The gradient coils 11, 12 are energised by application of an electric current by means of the power supply unit 21; to this end the power supply unit is fitted with electronic gradient amplification circuit that applies the electric current to the gradient coils so as to generate gradient pulses (also termed 'gradient waveforms') of appropriate temporal shape.

The strength, direction and duration of the gradients are controlled by control of the power supply unit. The magnetic resonance imaging system also includes transmission and receiving coils 13, 16 for generating the RF excitation pulses and for picking up the magnetic resonance signals, respectively. The transmission coil 13 is preferably constructed as a body coil 13 whereby (a part of) the object to be examined can be enclosed. The body coil is usually arranged in the magnetic resonance imaging system in such a manner that the patient 30 to be examined is enclosed by the body coil 13 when he or she is arranged in the magnetic resonance imaging system. The body coil 13 acts as a transmission antenna for the transmission of the RF excitation pulses and RF refocusing pulses. Preferably, the body coil 13 involves a spatially uniform intensity distribution of the transmitted RF pulses (RFS). The same coil or antenna is usually used alternately as the transmission coil and the receiving coil. Furthermore, the transmission and receiving coil is usually shaped as a coil, but other geometries where the transmission and receiving coil acts as a transmission and receiving antenna for RF electromagnetic signals are also feasible. The transmission and receiving coil 13 is connected to an electronic transmission and receiving circuit 15.

It is to be noted that it is alternatively possible to use separate receiving and/or transmission coils 16. For example, surface coils 16 can be used as receiving and/or transmission coils. Such surface coils have a high sensitivity in a comparatively small volume. The receiving coils, such as the surface coils, are connected to a demodulator 24 and the received magnetic resonance signals (MS) are demodulated by means of the demodulator 24. The demodulated magnetic resonance signals (DMS) are applied to a reconstruction unit. The receiving coil is connected to a preamplifier 23. The preamplifier 23 amplifies the RF resonance signal (MS) received by the receiving coil 16 and the amplified RF resonance signal is applied to a demodulator 24. The demodulator 24 demodulates the amplified RF resonance signal. The demodulated resonance signal contains the actual information concerning the local spin densities in the part of the object to be imaged. Furthermore, the transmission and receiving circuit 15 is connected to a modulator 22. The modulator 22 and the transmission and receiving circuit 15 activate the transmission coil 13 so as to transmit the RF excitation and refocusing pulses The reconstruction unit derives one or more image signals from the demodulated magnetic resonance signals (DMS), which image signals represent the image information of the imaged part of the object to be examined. The reconstruction unit 25 in practice is constructed preferably as a digital image processing unit 25 which is programmed so as to derive from the demodulated magnetic resonance signals the image signals which represent the image information of the part of the object to be imaged. The signal on the output of the reconstruction monitor 26, so that the monitor can display the magnetic resonance image. It is alternatively possible to store the signal from the reconstruction unit 25 in a buffer unit 27 while awaiting further processing.

The magnetic resonance imaging system according to the invention is also provided with a control unit 20, for example in the form of a computer which includes a (micro) processor. The control unit 20 controls the execution of the RF excitations and the application of the temporary gradient fields. To this end, the computer program according to the invention is loaded into the data processor or computer, for example, the control unit 20 and the reconstruction unit 25.

Further, one or more object motion sensors 41 are provided that can be placed on or attached to the body of the patient to be examined. The signals from these object motion sensors are applied to a motion detection and correction module 33 that is incorporated in the control unit 20. The motion detection and correction module 33 computes the motion correction for the magnetic resonance image from the received signals from the object motion sensors. Also RF antenna motion sensors 42 are provided on or integrated in the surface coils 16. The signals from the RF antenna motion sensors 42 area also applied to the motion detection and correction module 33. The motion detection and correction module computes the motion correction also on the basis of the motion and deformation of the surface coils 16. The signals form, the RF antenna motion detection represent the position and form (which can be deformed) of the electrically conducting receiver loop of the RF surface coil 16. Preferably, in this embodiment the surface coils are flexible, deformable RF surface coils. The signals from the object motion sensors 41 represent the position and shape of the part of the body of the patient to be examined to which the object motion sensors are mounted. Further, the motion detection and correction module is configured to compute the motion of the patient to be examined relative to the surface coils 16 and the RF body coil 13. That is, the motion detection and correction module computes the motion of the patient to be examined relative to the movement of the surface coils, e.g. as they move with the movement of the patient to be examined. The motion correction computed by the motion detection and correction module is applied to the reconstuctor that achieves that the reconstructed image is corrected for motion of the patient to be examined as well as motion and deformation of the surface coils 16.

Preferably, the object motion sensors as well as the RF antenna motion sensors are implemented as nano-motion sensors. for example 2-axis gyro devices or yaw axis devices may be employed.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A magnetic resonance examination system comprising:
   a flexible RF antenna configured to receive magnetic resonance signals from a patient to be examined, the flexible RF antenna being configured to be movably mounted to the patient such that the flexible RF antenna and the object are movable relative to each other;
   a first plurality of motion sensors mounted to the flexible RF antenna, and configured to detect motion and deformation of the flexible RF antenna;
   a second plurality of motion sensors configured to be directly mounted to the patient to detect motion of the object, the second plurality of motion sensors being separate from the first plurality of motion sensors; and
   a data processor connected with the first plurality of motion sensors and the second plurality of motion sensors and configured to:
      determine relative motion between the patient and the flexible RF antenna from the signals indicative of flexible RF antenna motion and deformations from the first plurality of motion sensors mounted to the flexible RF antenna and signals indicative of the motion of the patient from the second pluralities of motion sensors mounted to the patient; and
      reconstruct a motion and RF antenna deformation corrected magnetic resonance image from the received magnetic resonance signals corrected for the relative motion between the flexible RF antenna and the patient.

2. The magnetic resonance examination system as claimed in claim 1, wherein the first and second plurality of motion sensors include three axis micro-electro-magnetic switches (MEMS).

3. The magnetic resonance examination system as claimed in claim 1, further including a transmit and receive switch connected to an RF antenna and configured to supply RF signals to the RF antenna to operate the RF antenna as a transmit coil and to supply the received magnetic resonance signals to the data processor for reconstruction.

4. The magnetic resonance examination system as claimed in claim 1, wherein the flexible RF antenna is a surface RF coil.

5. The magnetic resonance examination system as claimed in claim 1, wherein:
   the flexible RF antenna is configured to be movably mounted relative to the object such that the flexible RF antenna is deformable and movable relative to the object;
   the data processor is configured to determine the deformation and the motion of the flexible RF antenna relative to the object from signals from the first and second pluralities of motion sensors, and to reconstruct the received magnetic resonance signals into a magnetic resonance image corrected for the relative information and motion of the flexible RF antenna relative to the object.

6. A magnetic resonance examination system comprising:
   a deformable local, surface RF coil configured to be mounted to an object to be examined such that the coil and the object are movable relative to each other, the local, surface RF coil being configured to at least receive magnetic resonance signals from the object, the local, surface RF coil including a rigid portion and a deformable portion;
   a first plurality of motion sensors mounted to the local, surface RF coil and configured to detect motion of the local, surface RF coil, the first plurality of motion sensors including sensors mounted to each of the rigid portion and the deformable portion of the local, surface RF coil;
   a second plurality of motion sensors configured to be mounted to the object to detect motion of the object;
   a data processor connected with the local, surface RF coil, the first plurality of motion sensors, and the second plurality of motion sensors, the data processor being configured to determine relative motion between the patient and the local surface RF coils and deformation of the deformable local, surface RF coil from the signals from the first and second pluralities of motion sensors and to reconstruct the received magnetic resonance signals into a magnetic resonance image that is both motion and deformation corrected.

7. The magnetic resonance examination system as claimed in claim 6, further including:
   a body coil configured to receive the object with the local, surface RF coil;
   the data processor being connected with the body coil and configured to control the body coil to generate RF excitation pulses and RF refocusing pulses.

8. The magnetic resonance examination system as claimed in claim 6, wherein the data processor determines both deformation of the deformable portion of the local, surface RF coil and the relative motion between the object and the local, surface RF coil and corrects the reconstructed image for both the deformation and the motion.

9. The magnetic resonance examination system as claimed in claim 6, further including:
   a modulator connected with the local surface RF coil and configured to control the local surface RF coil to generate magnetic resonance excitation and RF manipulation pulses in an excitation mode; and wherein the local, surface RF coil is configured to receive magnetic resonance signals in a receive mode, the data processor being configured to reconstruct the received magnetic signals into a motion and deformation corrected magnetic resonance image.

10. The magnetic resonance examination system as claimed in claim 6, wherein the first and second plurality of motion sensors include MEMS integrated circuits and wherein the MEMS integrated circuits of the first plurality of motion sensors are integrally connected to the local, surface RF coil.

11. The magnetic resonance examination system as claimed in claim 1, wherein the first plurality of motion sensors includes two-axis gyro nano devices.

12. The magnetic resonance examination system as claimed in claim 6, wherein the first plurality of motion sensors includes two-axis gyro nano devices.

13. The magnetic resonance examination system as claimed in claim 6, further including:
a monitor configured to display the magnetic resonance image.

14. The magnetic resonance examination system as claimed in claim 1, further including:
a monitor configured to display the magnetic resonance image.

15. A magnetic resonance examination system, comprising:
an RF antenna configured to receive magnetic resonance signals from an object to be examined;
a first plurality of motion sensors mounted to the RF antenna, and configured to detect motion of the RF antenna;
a second plurality of motion sensors attached to the object to detect motion of the object, the second plurality of motion sensors being separate from the first plurality of motion sensors; and
a data processor connected with the first plurality of motion sensors and the second plurality of motion sensors and configured to:
determine motion of the RF antenna using the first plurality of motion sensors mounted to the RF antenna;
determine motion of the object using the second plurality of motion sensors attached to the object;
determine relative motion between the object and the RF antenna using the first plurality of motion sensors mounted to the RF antenna and the second plurality of motion sensors attached to the object; and
reconstruct a motion corrected magnetic resonance image from the received magnetic resonance signals corrected for the relative motion between the RF antenna and the object.

16. The magnetic resonance examination system of claim 15 wherein the data processor is configured to determine the relative motion between the object and the RF antenna by:
determining motion of the RF antenna using the first plurality of motion sensors mounted to the RF antenna;
determining motion of the object using the second plurality of motion sensors attached to the object; and
determining the relative motion between the object and the RF antenna based on the determined motion of the RF antenna and the determined motion of the object.

* * * * *